Figure 1:
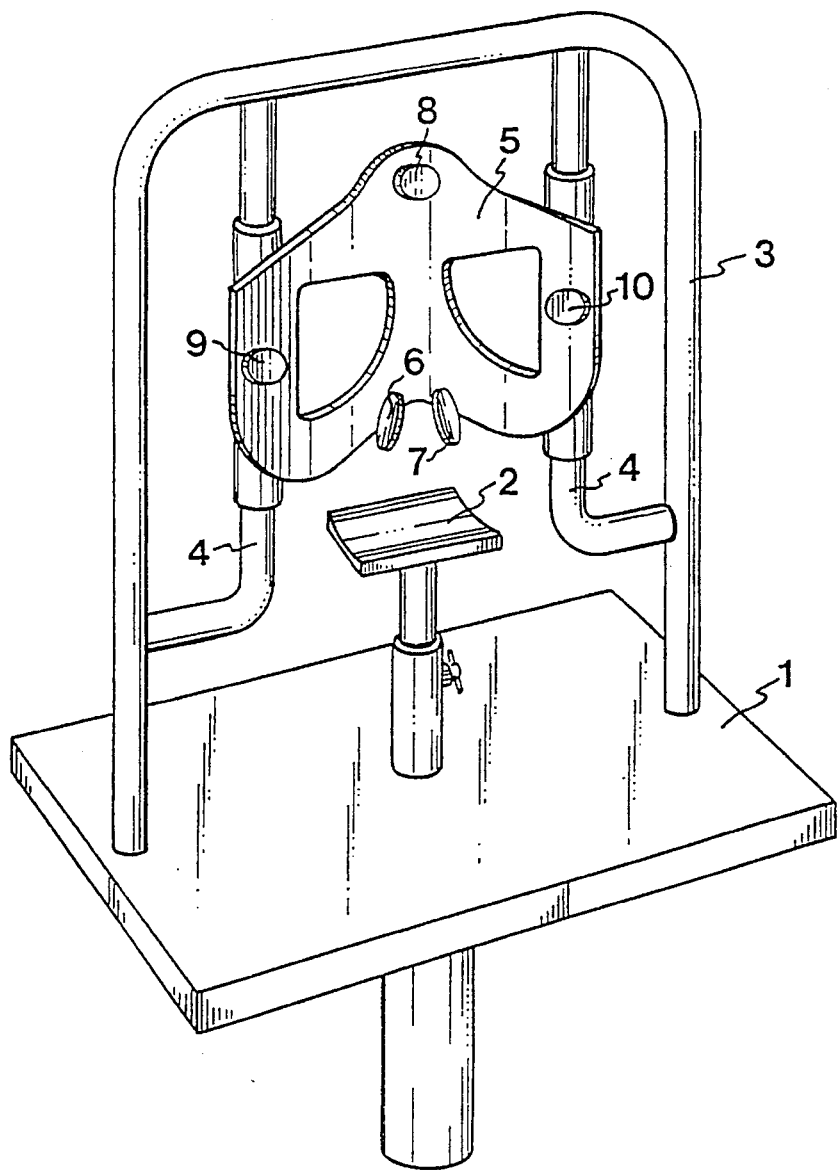

United States Patent [19]
Juto

[11] Patent Number: 5,591,175
[45] Date of Patent: Jan. 7, 1997

[54] DEVICE FOR POSITIONING A PERSON'S HEAD IN A COORDINATE SYSTEM

[76] Inventor: Jan-Erik Juto, Linnégatan 86, S-115 23, Stockholm, Sweden

[21] Appl. No.: 382,049
[22] PCT Filed: Aug. 12, 1993
[86] PCT No.: PCT/SE93/00669
  § 371 Date: Feb. 10, 1995
  § 102(e) Date: Feb. 10, 1995
[87] PCT Pub. No.: WO94/04076
  PCT Pub. Date: Mar. 3, 1994

[30] Foreign Application Priority Data

Aug. 12, 1992 [SE] Sweden ................................. 9202334

[51] Int. Cl.⁶ ............................ A61B 19/00; A61B 5/103
[52] U.S. Cl. ........................... 606/130; 128/774; 128/845
[58] Field of Search ............................ 606/130; 128/675, 128/672, 48, 845, 846, 857, 858, 774, 745, 782; 33/511, 512

[56] References Cited

U.S. PATENT DOCUMENTS 3,614,950 10/1971 Rabey .
3,658,054 4/1972 Iberall ..................................... 128/672
4,256,112 3/1981 Kopf et al. .
4,530,367 7/1985 Desjardinis et al. .
5,192,254 3/1993 Young ..................................... 128/782

*Primary Examiner*—Robert A. Hafer
*Assistant Examiner*—Benjamin Koo
*Attorney, Agent, or Firm*—Burns, Doane, Swecker & Mathis, L.L.P.

[57] ABSTRACT

In rhinostereometry, which is an optical method for measuring the congestion of the nasal mucosa, it has to be possible to repeatedly and with high accuracy fix the test subject's head in the same position in a coordinate system. This can be achieved by means of a fixing device comprising a plurality of pressure transducers (6–10) which are brought into contact with the test subject's head in such a manner that the head exerts at least a predetermined minimum pressure on all the transducers. Because the fixing device includes means for recording the positions of the pressure transducers in the coordinate system, the test subject's head can be repeatedly fixed in the same position.

4 Claims, 1 Drawing Sheet es being movable in the coordinate system and being adapted to be contacted with the person's head when fixing the person's head in the coordinate system;

DEVICE FOR POSITIONING A PERSON'S HEAD IN A COORDINATE SYSTEM

This invention relates to a device for fixing a person's head in a coordinate system.

Rhinostereometry is an optical method used for measuring the congestion of the nasal mucosa. The head of the person to be subjected to such measuring is fixed in a coordinate system. The positions in the coordinate system of a number of points on the nasal mucosa are determined by means of a surgical microscope which is placed on a micrometer table and is movable in all three dimensions.

In order for rhinostereometry to repeatedly yield comparable results, the head of the person subjected to such measuring has to be fixed in the same position on different occasions. Accurate fixation is of the utmost importance, since a point on the nasal mucosa moves about 4 mm at the most when the mucosa changes from a state of minimum congestion to one of maximum congestion.

The object of the invention is to provide a device enabling repeated and highly accurate fixation of a person's head in a coordinate system.

This object is achieved by a device having the distinctive features recited in appended claim 1. With the inventive device, a person's head can be fixed time after time in the same position in the coordinate system by setting the pressure transducers in previously recorded positions in the coordinate system and ensuring that each transducer is acted on by a predetermined pressure from the person's head.

Fixation is facilitated and can be done more quickly if the pressure transducers are disposed on a common support means which is movably arranged on a frame and thus can be used for roughly positioning the pressure transducers.

Preferably, the support means has the shape of a spectacle frame, two pressure transducers being arranged as pad bridges. In fixation, the pad bridges of the support means are moved downwards over the nasal bone as when glasses are put on.

Preferably, the remaining pressure transducers on the support means are so arranged as to be contacted with the forehead as well as the head close to the eyes during fixation. This arrangement of the pressure transducers is advantageous, in that the skull is here close beneath the skin, enabling more accurate fixation.

Figure 2:
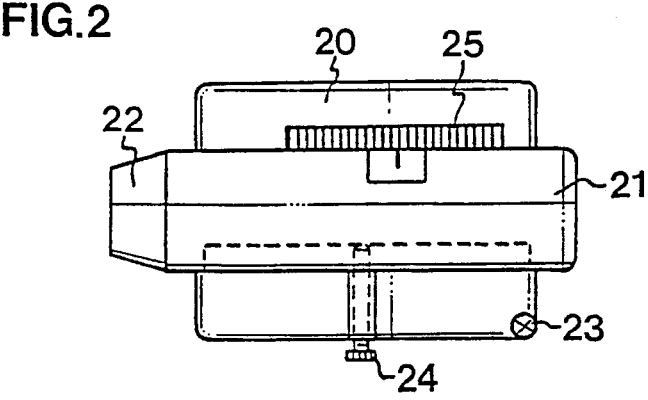

An embodiment of the invention will now be described in detail with reference to the accompanying drawing, in which FIG. 1 schematically illustrates an embodiment of a fixing device according to the invention; and FIG. 2 is an example of a pressure transducer to be used in the inventive device.

Thus, FIG. 1 shows an inventive fixing device comprising a vertically adjustable table 1, on which are mounted a vertically adjustable chin rest 2 and a fixed frame 3. Two limbs 4, on which a spectacle frame 5 is movably mounted, are fixedly arranged on the frame 3. The spectacle frame 5 can be fixed in different positions on the limbs 4, and its position thereon can be recorded by means provided therefor (not shown). Five pressure transducers 6–10 are mounted on the spectacle frame, but are merely schematically illustrated in the drawing in the form of "buttons". Two pressure transducers 6, 7 form pad bridges for the spectacle frame and are adapted to be contacted with the test subject's face at the nasal bone in the same manner as the pad bridges of ordinary glasses. A pressure transducer 8 is provided at the upper edge of the spectacle frame 5 so as to come into contact with the test subject's forehead when the pressure transducers 6, 7 in the form of pad bridges contact the nasal bone. The other two pressure transducers 9, 10 are provided at the side edges of the spectacle frame 5 and are adapted to come into contact with the test subject's face close to the eyes where the skull is just beneath the skin. For instance, the pressure transducers may have a surface of engagement with the face of about 3 mm². Naturally, the number of pressure transducers and their positions may vary.

FIG. 2 shows by way of example the design of a pressure transducer that may be used in the device of FIG. 1. The pressure transducer has a fixed holder 20, and a pressure-sensing unit 21 slidably mounted therein. The pressure-sensing unit 21 has a pressure-sensitive end portion 22 adapted to be contacted with the test subject's face. The pressure exerted by the face on the pressure-sensitive end portion 22 is recorded by means provided therefor (not shown), which emit a signal, e.g. turn on a light-emitting diode 23, when a given minimum pressure has been attained. A locking means 24 is adapted, in a first position, to fix the pressure-sensing unit 21 and, in a second position, to allow displacement of the pressure-sensing unit 21 in the holder 20. The position of the pressure-sensing unit 21 in the holder can be read on a scale 25 which is provided on the holder 20.

Naturally, the pressure transducers can be designed in many different ways. The main thing is that the positions of the pressure transducers in the coordinate system can be recorded and a signal be obtained when the test subject's head exerts at least a predetermined minimum pressure on the transducers. Advantageously, the pressure transducers are connected to a means that indicates when at least the predetermined minimum pressure is exerted on all the pressure transducers.

When a test subject is to undergo rhinostereometry for the first time, he puts the chin against the chin rest 2, and the spectacle frame 5 is moved downwards so as to apply the pressure transducers 6, 7 against the nasal bone with at least a predetermined minimum pressure. Then, the other pressure transducers 8–10 are so set that the minimum pressure is attained. The position of the spectacle frame 5 on the limbs 4 is recorded, as are the positions of the pressure transducers 6–10.

When the test subject is again to undergo rhinostereometry and comparable results are to be obtained, the spectacle frame 5 is placed on the limbs 4 in the position previously recorded. Also the pressure transducers 6–10 are arranged in the positions previously recorded. Thereafter, the test subject puts his face against the spectacle frame, so that all the pressure transducers indicate that the minimum pressure has been attained, the test subject's face being now fixed in the same position in the coordinate system as in the first measurement, enabling comparable results to be obtained.

I claim:

1. A device for fixing a person's head in a coordinate system, comprising:

a plurality of pressure transducers, the pressure transducers being movable in the coordinate system and being adapted to be contacted with the person's head when fixing the person's head in the coordinate system;

means, associated with each of the pressure transducers, for detecting when the transducers are acted on by at least one predetermined pressure from the person's head;

support means on which the plurality of pressure transducers is fixed;

a frame fixedly arranged in the coordinate system, the support means being movably mounted on the frame; and means for recording positions of the pressure transducers in the coordinate system, wherein the support means has the shape of a spectacle frame having two eye holes and two pressure transducers, the two pressure transducers being arranged as pad bridges to be contacted with a nasal bone of the person's head by moving the nasal bone of the person's head into contact with the two pressure transducers.

2. A device as set forth in claim 1, at least one of the pressure transducers is so positioned on the support means as to be contacted with a forehead of the person's head during fixation of the person's head in the coordinate system, and at least two of the pressure transducers are so positioned on the support means as to be contacted with regions of the person's head close to the eyes.

3. A device as set forth in claim 1, wherein the detecting means associated with the pressure transducers are connected to an indicator means for indicating when all the transducers are acted on by at least the predetermined pressure.

4. A device as set forth in claim 2, wherein the detecting means associated with the pressure transducers are connected to an indicator means for indicating when all the transducers are acted on by at least the predetermined pressure.

* * * * *